(12) United States Patent
Salvi et al.

(10) Patent No.: US 8,231,387 B2
(45) Date of Patent: Jul. 31, 2012

(54) POROUS IMPLANT WITH NON-POROUS THREADS

(75) Inventors: Joseph A. Salvi, Chula Vista, CA (US); Shahram Zamani, Poway, CA (US); Mojtaba Esfahani, Del Mar, CA (US)

(73) Assignee: Zimmer, Inc., Warsaw, IN (US)

( * ) Notice: Subject to any disclaimer, the term of this patent is extended or adjusted under 35 U.S.C. 154(b) by 489 days.

(21) Appl. No.: 12/167,107

(22) Filed: Jul. 2, 2008

(65) Prior Publication Data

US 2010/0003639 A1    Jan. 7, 2010

(51) Int. Cl.
*A61C 8/00* (2006.01)

(52) U.S. Cl. ........................................ 433/174

(58) Field of Classification Search .......... 433/172–176, 433/201.1, 202.1, 215, 220, 224; 623/16.11, 623/20.34, 20.36, 23.34, 23.46; 606/301, 606/306, 310, 316, 312, 328, 331, 232; 411/438, 411/425, 392, 383, 395, 396
See application file for complete search history.

(56) References Cited

U.S. PATENT DOCUMENTS

| | | | |
|---|---|---|---|
| 2,721,387 A | 10/1955 | Ashuckian | |
| 3,314,420 A | 4/1967 | Smith et al. | |
| 3,423,830 A | 1/1969 | Halpern et al. | |
| 3,423,831 A | 1/1969 | Semmelman | |
| 3,435,526 A * | 4/1969 | Brancato | 433/174 |
| 3,497,953 A | 3/1970 | Weissman | |
| 3,685,115 A | 8/1972 | Scott | |
| 3,713,860 A | 1/1973 | Auskern | |
| 3,740,851 A | 6/1973 | Weissman | |
| 3,797,113 A | 3/1974 | Brainin | |
| 3,849,887 A | 11/1974 | Brainin | |
| 3,896,547 A | 7/1975 | Kulwiec | |
| 3,905,109 A | 9/1975 | Cohen et al. | |
| 3,906,550 A | 9/1975 | Rostoker | |
| 3,919,773 A | 11/1975 | Freeman | |
| 3,934,347 A | 1/1976 | Lash et al. | |
| 3,992,725 A | 11/1976 | Homsy | |
| 4,011,602 A | 3/1977 | Rybicki et al. | |
| 4,016,651 A | 4/1977 | Kawahara et al. | |
| 4,086,701 A | 5/1978 | Kawahara et al. | |
| 4,097,935 A | 7/1978 | Jarcho | |

(Continued)

FOREIGN PATENT DOCUMENTS

CA    2506845 A1    7/2004

(Continued)

OTHER PUBLICATIONS

An Introduction to Silanes and Their Clinical Applications in Dentistry, Jukka P.I Matinlinna et al., vol. 17, No. 2, pp. 155-164 The International Journal of Prosthodontics, 2004.

(Continued)

*Primary Examiner* — Heidi M Eide
(74) *Attorney, Agent, or Firm* — Schwegman, Lundberg & Woessner, P.A.

(57) ABSTRACT

An implant which includes a shaft made of a first material and having an exterior surface, and at least one thread made of a second material different from the first material, engaging the exterior surface, and extending outwardly from the exterior surface for engaging bone. After implantation of the implant, bone tissue may osseointegrate into the porous shaft to anchor the implant within the surrounding bone. The first material may be a porous metal and include tantalum while the second material is non-porous.

26 Claims, 2 Drawing Sheets

U.S. PATENT DOCUMENTS

| | | | |
|---|---|---|---|
| 4,122,605 A | 10/1978 | Hirabayashi et al. | |
| 4,131,597 A | 12/1978 | Bluethgen | |
| 4,178,686 A | 12/1979 | Riess et al. | |
| 4,195,366 A | 4/1980 | Jarcho et al. | |
| 4,199,864 A | 4/1980 | Ashman | |
| 4,229,170 A | 10/1980 | Perez | |
| 4,244,689 A | 1/1981 | Ashman | |
| 4,252,525 A | 2/1981 | Child | |
| 4,259,072 A | 3/1981 | Hirabayashi et al. | |
| 4,281,991 A | 8/1981 | Michi et al. | |
| 4,321,042 A | 3/1982 | Scheicher | |
| 4,375,967 A | 3/1983 | Schaeffer | |
| 4,379,694 A | 4/1983 | Riess | |
| 4,381,918 A | 5/1983 | Ehmford | |
| 4,411,624 A | 10/1983 | Ogino et al. | |
| 4,431,420 A | 2/1984 | Adair | |
| 4,439,152 A | 3/1984 | Small | |
| 4,448,758 A | 5/1984 | Nagai et al. | |
| 4,475,892 A | 10/1984 | Faunce | |
| 4,478,904 A | 10/1984 | Ducheyne et al. | |
| 4,483,678 A | 11/1984 | Nishio et al. | |
| 4,492,577 A | 1/1985 | Farris et al. | |
| 4,531,915 A | 7/1985 | Tatum, Jr. | |
| 4,531,916 A | 7/1985 | Scantlebury et al. | |
| 4,536,158 A | 8/1985 | Bruins et al. | |
| 4,548,959 A | 10/1985 | Nagai et al. | |
| 4,556,534 A | 12/1985 | Burnett | |
| 4,708,652 A | 11/1987 | Fujiu et al. | |
| 4,713,006 A | 12/1987 | Hakamatsuka et al. | |
| 4,722,688 A | 2/1988 | Lonca | |
| 4,731,085 A | 3/1988 | Koch | |
| 4,737,411 A | 4/1988 | Graves, Jr. et al. | |
| 4,743,260 A | 5/1988 | Burton | |
| 4,744,757 A | 5/1988 | Adair et al. | |
| 4,744,759 A | 5/1988 | Bowen | |
| 4,820,157 A | 4/1989 | Salvo | |
| 4,842,517 A | 6/1989 | Kawahara et al. | |
| 4,871,384 A | 10/1989 | Kasuga | |
| 4,872,839 A | 10/1989 | Brajnovic | |
| 4,872,840 A | 10/1989 | Bori | |
| 4,877,400 A | 10/1989 | Holsclaw | |
| 4,880,610 A | 11/1989 | Constantz | |
| 4,906,190 A | 3/1990 | Michna | |
| 4,909,738 A | 3/1990 | Ai et al. | |
| 4,957,554 A | 9/1990 | Mathers et al. | |
| 4,957,819 A | 9/1990 | Kawahara et al. | |
| 4,960,733 A | 10/1990 | Kasuga et al. | |
| 4,969,817 A | 11/1990 | Hiranuma et al. | |
| 4,969,913 A | 11/1990 | Ojima | |
| 4,983,182 A | 1/1991 | Kijima et al. | |
| 5,000,685 A | 3/1991 | Brajnovic | |
| 5,002,488 A * | 3/1991 | Homsy | 433/169 |
| 5,004,421 A | 4/1991 | Lazarof | |
| 5,007,835 A | 4/1991 | Valen | |
| 5,009,709 A | 4/1991 | Ibsen et al. | |
| 5,049,074 A | 9/1991 | Otani et al. | |
| 5,055,497 A | 10/1991 | Okada et al. | |
| 5,061,285 A | 10/1991 | Koch | |
| 5,062,798 A | 11/1991 | Tsuge et al. | |
| 5,064,731 A | 11/1991 | Miyazaki et al. | |
| 5,076,789 A | 12/1991 | Tanaka | |
| 5,087,200 A | 2/1992 | Brajnovic et al. | |
| 5,120,340 A | 6/1992 | Ducheyne et al. | |
| 5,123,844 A | 6/1992 | Wakai et al. | |
| 5,125,839 A | 6/1992 | Ingber et al. | |
| 5,125,971 A | 6/1992 | Nonami et al. | |
| 5,139,424 A | 8/1992 | Yli-Urpo | |
| 5,152,687 A | 10/1992 | Amino | |
| 5,176,747 A | 1/1993 | Panzera et al. | |
| 5,180,303 A | 1/1993 | Hornburg et al. | |
| 5,186,626 A | 2/1993 | Tanaka | |
| 5,192,325 A | 3/1993 | Kijima et al. | |
| 5,194,000 A | 3/1993 | Dury | |
| 5,194,001 A | 3/1993 | Salvo | |
| 5,199,873 A | 4/1993 | Schulte et al. | |
| 5,205,745 A | 4/1993 | Kamiya et al. | |
| 5,232,365 A | 8/1993 | Ikehara | |
| 5,232,878 A | 8/1993 | Kasuga et al. | |
| 5,236,458 A | 8/1993 | Ducheyne et al. | |
| 5,238,405 A | 8/1993 | Marlin | |
| 5,254,005 A | 10/1993 | Zuest | |
| 5,282,861 A | 2/1994 | Kaplan | |
| 5,282,863 A | 2/1994 | Burton | |
| 5,288,232 A | 2/1994 | Panzera et al. | |
| 5,306,673 A | 4/1994 | Hermansson et al. | |
| 5,308,391 A | 5/1994 | Komma et al. | |
| 5,310,343 A | 5/1994 | Hasegawa et al. | |
| 5,312,254 A | 5/1994 | Rosenlicht | |
| 5,314,334 A | 5/1994 | Panzera et al. | |
| 5,342,201 A | 8/1994 | Oden | |
| 5,344,318 A | 9/1994 | Wilson et al. | |
| 5,344,457 A | 9/1994 | Pilliar et al. | |
| 5,346,397 A | 9/1994 | Braiman | |
| 5,415,546 A | 5/1995 | Cox, Sr. | |
| 5,419,702 A | 5/1995 | Beaty et al. | |
| 5,425,640 A | 6/1995 | Scharf | |
| 5,439,380 A | 8/1995 | Marlin | |
| 5,443,515 A | 8/1995 | Cohen et al. | |
| 5,449,291 A | 9/1995 | Lueschen et al. | |
| 5,458,488 A * | 10/1995 | Chalifoux | 433/173 |
| 5,468,544 A | 11/1995 | Marcolongo et al. | |
| 5,470,230 A | 11/1995 | Daftary et al. | |
| 5,476,383 A | 12/1995 | Beaty et al. | |
| 5,549,123 A | 8/1996 | Okuyama et al. | |
| 5,554,665 A | 9/1996 | Tateosian et al. | |
| 5,562,733 A | 10/1996 | Weissbach et al. | |
| 5,571,016 A | 11/1996 | Ingber et al. | |
| 5,572,652 A | 11/1996 | Robusto et al. | |
| 5,575,652 A | 11/1996 | Gaffar et al. | |
| 5,584,693 A | 12/1996 | Nishihara | |
| 5,591,030 A | 1/1997 | Thiel et al. | |
| 5,612,049 A | 3/1997 | Li et al. | |
| 5,614,330 A | 3/1997 | Panzera et al. | |
| 5,621,035 A | 4/1997 | Lyles et al. | |
| 5,624,262 A | 4/1997 | Yarovesky et al. | |
| 5,645,934 A | 7/1997 | Marcolongo et al. | |
| 5,674,069 A | 10/1997 | Osorio | |
| 5,676,745 A | 10/1997 | Kelly et al. | |
| 5,683,249 A | 11/1997 | Ibsen et al. | |
| 5,685,714 A | 11/1997 | Beaty et al. | |
| 5,695,337 A | 12/1997 | Tyszbiat Sadoun | |
| 5,697,785 A | 12/1997 | Delahaye | |
| 5,697,976 A | 12/1997 | Chesterfield et al. | |
| 5,697,997 A | 12/1997 | Aronsson et al. | |
| 5,698,019 A | 12/1997 | Frank et al. | |
| 5,713,994 A | 2/1998 | Kramer et al. | |
| 5,723,007 A | 3/1998 | Engel et al. | |
| 5,727,943 A | 3/1998 | Beaty et al. | |
| 5,755,809 A | 5/1998 | Cohen et al. | |
| 5,759,036 A | 6/1998 | Hinds | |
| 5,762,500 A | 6/1998 | Lazarof | |
| 5,772,438 A | 6/1998 | Deom | |
| 5,775,912 A | 7/1998 | Panzera et al. | |
| 5,785,524 A | 7/1998 | Wolf | |
| 5,833,463 A | 11/1998 | Hurson | |
| 5,833,464 A | 11/1998 | Foser | |
| 5,839,900 A | 11/1998 | Billet et al. | |
| 5,843,348 A | 12/1998 | Giordano | |
| 5,849,068 A | 12/1998 | Hofmann et al. | |
| 5,873,721 A | 2/1999 | Willoughby | |
| 5,910,273 A | 6/1999 | Thiel et al. | |
| 5,915,967 A | 6/1999 | Clokie | |
| 5,925,180 A | 7/1999 | Frank et al. | |
| 5,931,674 A | 8/1999 | Hanosh et al. | |
| 5,934,906 A | 8/1999 | Phimmasone | |
| 5,939,211 A | 8/1999 | Mormann | |
| 5,947,732 A | 9/1999 | Beaty et al. | |
| 5,947,737 A | 9/1999 | Billet et al. | |
| 5,951,290 A | 9/1999 | Ardizio et al. | |
| 5,951,293 A | 9/1999 | Billet et al. | |
| 5,951,295 A | 9/1999 | Lyles et al. | |
| 5,964,592 A | 10/1999 | Hites et al. | |
| 5,971,760 A | 10/1999 | Letcher | |
| 5,975,905 A | 11/1999 | Kim et al. | |
| 5,984,683 A | 11/1999 | Sakata et al. | |
| 5,989,026 A | 11/1999 | Rogers et al. | |
| 5,989,027 A | 11/1999 | Wagner et al. | |

| | | |
|---|---|---|
| 6,010,337 A | 1/2000 | Billet et al. |
| 6,012,923 A | 1/2000 | Bassett et al. |
| 6,013,591 A | 1/2000 | Ying et al. |
| 6,027,742 A | 2/2000 | Lee et al. |
| 6,039,568 A | 3/2000 | Hinds |
| 6,045,361 A | 4/2000 | Misch et al. |
| 6,048,203 A | 4/2000 | Rosenberg |
| 6,048,205 A | 4/2000 | Wright |
| 6,054,400 A | 4/2000 | Brink et al. |
| RE36,689 E | 5/2000 | Beaty et al. |
| 6,056,547 A | 5/2000 | Names |
| 6,063,442 A | 5/2000 | Cohen et al. |
| 6,080,692 A | 6/2000 | Reise et al. |
| 6,087,553 A | 7/2000 | Cohen et al. |
| 6,117,456 A | 9/2000 | Lee et al. |
| 6,120,293 A | 9/2000 | Lazzara et al. |
| 6,126,445 A | 10/2000 | Willoughby |
| 6,126,732 A | 10/2000 | Hofmann et al. |
| 6,132,214 A * | 10/2000 | Suhonen et al. ............ 433/201.1 |
| 6,135,775 A | 10/2000 | Weisman |
| 6,146,423 A | 11/2000 | Cohen et al. |
| 6,152,737 A | 11/2000 | Beaty et al. |
| 6,159,010 A | 12/2000 | Rogers et al. |
| 6,159,417 A | 12/2000 | Giordano |
| 6,168,435 B1 | 1/2001 | Beaty et al. |
| 6,168,436 B1 | 1/2001 | O'Brien |
| 6,168,633 B1 | 1/2001 | Shoher et al. |
| 6,183,256 B1 | 2/2001 | Fisher et al. |
| 6,183,515 B1 | 2/2001 | Barlow et al. |
| 6,186,791 B1 | 2/2001 | Karmaker et al. |
| 6,193,516 B1 | 2/2001 | Story |
| 6,200,137 B1 | 3/2001 | Holand et al. |
| 6,206,192 B1 | 3/2001 | Winstead et al. |
| 6,213,775 B1 * | 4/2001 | Reipur ......................... 433/173 |
| 6,214,368 B1 | 4/2001 | Lee et al. |
| 6,224,662 B1 | 5/2001 | Nemeth |
| 6,244,869 B1 | 6/2001 | Billet et al. |
| 6,250,922 B1 | 6/2001 | Bassett et al. |
| 6,267,597 B1 | 7/2001 | Kim |
| 6,270,347 B1 | 8/2001 | Webster et al. |
| 6,271,282 B1 | 8/2001 | Giordano |
| 6,280,863 B1 | 8/2001 | Frank et al. |
| 6,283,753 B1 | 9/2001 | Willoughby |
| 6,287,341 B1 | 9/2001 | Lee et al. |
| 6,299,448 B1 | 10/2001 | Zdrahala et al. |
| 6,306,784 B1 | 10/2001 | Drescher et al. |
| 6,322,728 B1 | 11/2001 | Brodkin et al. |
| 6,325,628 B1 | 12/2001 | Morgan |
| 6,331,312 B1 | 12/2001 | Lee et al. |
| 6,342,302 B1 | 1/2002 | Steidl et al. |
| 6,342,458 B1 | 1/2002 | Scweiger et al. |
| 6,343,930 B1 | 2/2002 | Beaty et al. |
| 6,345,984 B2 | 2/2002 | Karmaker et al. |
| 6,354,836 B1 | 3/2002 | Panzera et al. |
| 6,362,250 B1 | 3/2002 | Karmaker et al. |
| 6,362,251 B1 | 3/2002 | Alkemper et al. |
| 6,379,153 B1 | 4/2002 | Schroering |
| 6,386,876 B1 | 5/2002 | Lee |
| 6,394,806 B1 | 5/2002 | Kumar |
| 6,402,517 B1 | 6/2002 | Hozumi et al. |
| 6,419,491 B1 | 7/2002 | Ricci et al. |
| 6,431,868 B2 | 8/2002 | Story |
| 6,439,890 B1 | 8/2002 | Karmaker et al. |
| 6,447,549 B1 | 9/2002 | Taft |
| 6,450,813 B1 | 9/2002 | McDonald et al. |
| 6,451,292 B2 | 9/2002 | Warford, III et al. |
| 6,454,569 B1 | 9/2002 | Hollander et al. |
| 6,485,849 B2 | 11/2002 | Petticrew |
| 6,495,073 B2 | 12/2002 | Bodenmiller et al. |
| 6,497,573 B2 | 12/2002 | Wagner et al. |
| 6,503,625 B1 | 1/2003 | Rieder et al. |
| 6,514,453 B2 | 2/2003 | Vigliotti et al. |
| 6,527,553 B2 | 3/2003 | Yeung |
| 6,540,784 B2 | 4/2003 | Barlow et al. |
| 6,627,327 B2 | 9/2003 | Reidt et al. |
| 6,641,775 B2 | 11/2003 | Vigliotti et al. |
| 6,648,645 B1 | 11/2003 | MacDougald et al. |
| 6,666,684 B1 | 12/2003 | Names |
| 6,669,476 B2 | 12/2003 | Prestipino et al. |
| 6,679,701 B1 | 1/2004 | Blacklock |
| 6,689,202 B2 | 2/2004 | Panzera |
| 6,743,936 B1 | 6/2004 | Wellinghoff et al. |
| 6,752,863 B2 | 6/2004 | Lyles et al. |
| 6,755,651 B2 | 6/2004 | Brodbeck |
| 6,787,584 B2 | 9/2004 | Jia et al. |
| 6,797,006 B2 | 9/2004 | Hodorek |
| 6,808,659 B2 | 10/2004 | Schulman et al. |
| 6,821,462 B2 | 11/2004 | Schulman et al. |
| 6,846,181 B2 | 1/2005 | Karmaker et al. |
| 6,878,456 B2 | 4/2005 | Castro et al. |
| 6,881,488 B2 | 4/2005 | Giordano |
| 6,916,177 B2 * | 7/2005 | Lin et al. ....................... 433/173 |
| 6,932,606 B2 | 8/2005 | Aravena et al. |
| 6,945,448 B2 | 9/2005 | Medlin et al. |
| 6,949,251 B2 | 9/2005 | Dalal et al. |
| 6,953,594 B2 | 10/2005 | Lee et al. |
| 6,976,999 B2 | 12/2005 | Charlebois et al. |
| 6,984,261 B2 | 1/2006 | Cummings et al. |
| 6,986,660 B2 | 1/2006 | Kumar et al. |
| 6,994,726 B2 * | 2/2006 | Lin et al. ..................... 623/16.11 |
| 7,011,522 B2 | 3/2006 | Panzera et al. |
| 7,291,012 B2 | 11/2007 | Lyren |
| 2001/0000486 A1 | 4/2001 | Story |
| 2001/0051832 A1 | 12/2001 | Bakker et al. |
| 2002/0028424 A1 | 3/2002 | Prestipino et al. |
| 2002/0039718 A1 | 4/2002 | Kwan |
| 2002/0076673 A1 | 6/2002 | Wagner et al. |
| 2002/0095213 A1 | 7/2002 | Bakker et al. |
| 2002/0115742 A1 | 8/2002 | Trieu et al. |
| 2002/0155412 A1 | 10/2002 | Panzera et al. |
| 2002/0160334 A1 | 10/2002 | Brodbeck |
| 2003/0031984 A1 | 2/2003 | Rusin et al. |
| 2003/0068598 A1 | 4/2003 | Vallittu et al. |
| 2003/0073394 A1 | 4/2003 | Reidt et al. |
| 2003/0087984 A1 | 5/2003 | Erbe et al. |
| 2003/0096214 A1 | 5/2003 | Luthardt et al. |
| 2003/0134925 A1 | 7/2003 | Guzauskas |
| 2003/0148247 A1 | 8/2003 | Sicurelli et al. |
| 2004/0024081 A1 | 2/2004 | Trieu et al. |
| 2004/0058299 A1 | 3/2004 | Molin et al. |
| 2004/0064192 A1 | 4/2004 | Bubb |
| 2004/0097627 A1 | 5/2004 | Vallittu et al. |
| 2004/0106085 A1 | 6/2004 | Vallittu et al. |
| 2004/0106087 A1 | 6/2004 | Weigl et al. |
| 2004/0131562 A1 | 7/2004 | Gower et al. |
| 2004/0152034 A1 | 8/2004 | Cummings et al. |
| 2004/0170946 A1 | 9/2004 | Lyren |
| 2004/0197737 A1 | 10/2004 | Uckelmann et al. |
| 2004/0234925 A1 | 11/2004 | Benhamou |
| 2004/0241614 A1 | 12/2004 | Goldberg et al. |
| 2005/0014108 A1 | 1/2005 | Wohrle et al. |
| 2005/0023710 A1 | 2/2005 | Brodkin et al. |
| 2005/0028424 A1 | 2/2005 | Poinski |
| 2005/0031704 A1 | 2/2005 | Ahn |
| 2005/0084533 A1 | 4/2005 | Howdle et al. |
| 2005/0084819 A1 | 4/2005 | Sims et al. |
| 2005/0084821 A1 | 4/2005 | Sims et al. |
| 2005/0096652 A1 | 5/2005 | Burton |
| 2005/0100724 A1 | 5/2005 | Seargeant |
| 2005/0109060 A1 | 5/2005 | Cummings et al. |
| 2005/0123672 A1 | 6/2005 | Justin et al. |
| 2005/0184134 A1 | 8/2005 | Charlebois et al. |
| 2005/0191248 A1 | 9/2005 | Hunter et al. |
| 2005/0221259 A1 | 10/2005 | Anderson |
| 2005/0261795 A1 | 11/2005 | Ghosh et al. |
| 2005/0266382 A1 | 12/2005 | Soler et al. |
| 2006/0075826 A1 | 4/2006 | Roberts et al. |
| 2007/0015110 A1 | 1/2007 | Zhang |
| 2007/0020582 A1 | 1/2007 | Neumeyer |
| 2007/0111165 A1 | 5/2007 | Wallick |
| 2007/0118221 A1 | 5/2007 | Robie et al. |
| 2007/0148621 A1 | 6/2007 | Yakir |
| 2007/0184265 A1 | 8/2007 | Ranganathan et al. |
| 2008/0050699 A1 | 2/2008 | Zhang |
| 2008/0241793 A1 | 10/2008 | Collins |
| 2009/0036908 A1 | 2/2009 | Zokol et al. |
| 2009/0098510 A1 | 4/2009 | Zhang |
| 2009/0098511 A1 | 4/2009 | Zhang |

FOREIGN PATENT DOCUMENTS

| | | |
|---|---|---|
| DE | 4209569 C2 | 9/1993 |
| DE | 19529036 A1 | 3/1997 |
| DE | 10105398 A1 | 8/2002 |
| EP | 0266313 | 5/1988 |
| EP | 0271236 | 6/1988 |
| EP | 0345581 A2 | 12/1989 |
| EP | 0366018 B1 | 5/1990 |
| EP | 0417018 B1 | 3/1991 |
| EP | 0467948 | 1/1992 |
| EP | 0498923 | 8/1992 |
| EP | 0333503 | 2/1993 |
| EP | 0560279 | 9/1993 |
| EP | 0806211 | 11/1997 |
| EP | 0950421 | 10/1999 |
| EP | 1281372 | 2/2003 |
| EP | 1598028 | 11/2005 |
| EP | 1712205 | 10/2006 |
| GB | 1526780 | 9/1978 |
| GB | 2401867 | 11/2004 |
| GB | 2416996 A1 | 2/2006 |
| JP | 61275205 | 12/1986 |
| JP | 1025849 A | 1/1989 |
| JP | 63290559 | 11/1998 |
| JP | 2002126071 A | 5/2002 |
| WO | 8900410 | 1/1989 |
| WO | 9011979 | 11/1990 |
| WO | 9320773 | 10/1993 |
| WO | 9421190 | 9/1994 |
| WO | 9528973 | 11/1995 |
| WO | 9721393 | 6/1997 |
| WO | 9741809 | 11/1997 |
| WO | 9830170 | 7/1998 |
| WO | 0021455 | 4/2000 |
| WO | 0132072 | 5/2001 |
| WO | 0187193 | 11/2001 |
| WO | 0234155 | 5/2002 |
| WO | 0236039 | 5/2002 |
| WO | 02062901 | 8/2002 |
| WO | 02064100 | 8/2002 |
| WO | 03065939 | 8/2003 |
| WO | 03065996 | 8/2003 |
| WO | 03078508 | 9/2003 |
| WO | 03094774 | 11/2003 |
| WO | 2004054464 | 7/2004 |
| WO | 2007027794 | 3/2006 |
| WO | 2006022610 | 8/2006 |
| WO | 2007027794 | 3/2007 |
| WO | WO 2007025290 * | 3/2007 |
| WO | 2007/086832 A2 | 8/2007 |
| WO | 2007086832 | 8/2007 |

OTHER PUBLICATIONS

Computer-Guided Immediate Provisionalization of Anterior Multiple Adjacent Implants: Surgical and Prosthodontic Rationale, Joseph Y. K. Kan, Practical Procedures & Aethetic Dentistry, vol. 18, No. 10, 617-623, 2006.

Flocculants, Binders, and Bonds, Chapter 11, Molecular Binders pp. 173-177, 1995.

Innovative Ceramic-Fiber Technology Energizes Advanced Cerametrics, Richard B. Cass et al. Story—the American Ceramic Society, American Ceramics Society Bulletin, Nov. 2003, pp. 9701-9706.

Presurgical Planning With CT-Derived Fabrication of Surgical Guides, Scott D. Ganz, J Oral Maxillofac Surg 63:59-73, 2005, Suppl 2.

Prosthetically Directed Implant Placement ing Computer Software to Ensure Precise Placement and Predictable Prosthetic Outcomes. Part 1: Diagnostics, Imaging, and Collaborative Accountability, Alan L. Rosenfeld, International Journal of Periodontics & Restorative Dentistry, vol. 26, No. 3, 2006, 215-221.

Shape Optimization of Randomly Oriented Short Fibers for Bone Cement Reinforcements, Yan Zhou, Chaodi Li, James J. Mason, Materials Science & Engineering A 393 (2005) 374-381.

The Clinical Assessment of a Ceramic-Coated Transmucosal Dental Implant Collar; International Journal of Prosthodonics; 1996—vol. 9, Issue 5; pp. 466-472.

Two Applications of Transmucosal Milled Ceramic in Implantology; Preliminary Clinical Examples; Implant Quintessence Dentistry International; Aug. 1996—vol. 27, Issue 8, pp. 533-547.

International Search Report from related application PCT/2006/033893, dated Jan. 29, 2007, 1 page.

International Search Report from related application PCT/2006/020130, dated Feb. 6, 2007, 10 pages.

International Search Report from related application PCT/2007/069562, dated Jul. 7, 2008, 1 page.

International Search Report from related application PCT/2008/074616; dated Dec. 16, 2008; 4 pages.

International Search Report from related application PCT/2008/074645, dated Dec. 29, 2008; 9 pages.

International Search Report from related application PCT/2008/074642; dated Feb. 12, 2009. 4 pages.

International Search Report from related application PCT/2008/074655; dated Feb. 18, 2009. 9 pages.

International Search Report from related application PCT/US2009/048469; dated Oct. 19, 2009, 9 pages.

International Search Report from related application PCT/2009/048478; dated Dec. 10, 2009: 13 pages.

International Search Report from related application PCT/2009/062308; dated Jan. 21, 2010: 17 pages.

International Search Report from related application PCT/2009/048456; dated Apr. 27, 2010; 5 pages.

PEEK-CLASSIX; information Sheet Invibio Ltd., Properties of PEEK-CLASSIX, White Granular, Nov. 2003.

Related PCT Search Report from related application No. PCT/US2009/048481; dated Dec. 10, 2009; 10 pages.

* cited by examiner

POROUS IMPLANT WITH NON-POROUS THREADS

BACKGROUND OF THE INVENTION

1. Field of the Invention

The present invention relates to bone implants and, in particular, to a threaded dental implant with improved osseointegration.

2. Description of the Related Art

Dental implants are commonly used as anchoring members for dental restorations to provide prosthetic teeth at one or more edentulous sites in a patient's dentition at which the patient's original teeth have been lost or damaged. Typically, known implant systems include a dental implant made from a suitable biocompatible material, such as titanium. The dental implant is typically threaded into a bore which is drilled into the patient's mandible or maxilla at the edentulous site. The implant provides an anchoring member for a dental abutment, which in turn provides an interface between the implant and a dental restoration. The restoration is typically a porcelain crown fashioned according to known methods.

Many current dental implant surgeries are performed in two stages. In the initial or first stage, an incision is made in the patient's gingiva at an edentulous side, and a bore is drilled into the patient's mandible or maxilla at the edentulous site, followed by threading or impacting a dental implant into the bore using a suitable driver. Thereafter, a cap is fitted onto the implant to close the abutment coupling structure of the implant, and the gingiva is sutured over the implant. Over a period of several months, the patient's jaw bone grows around the implant to securely anchor the implant in the surrounding bone, a process known as osseointegration.

In a second stage of the procedure following osseointegration, the dentist reopens the gingiva at the implant site and secures an abutment and optionally, a temporary prosthesis or temporary healing member, to the implant. Then, a suitable permanent prosthesis or crown is fashioned, such as from one or more impressions taken of the abutment and the surrounding gingival tissue and dentition. In the final stage, the temporary prosthesis or healing member is removed and replaced with the permanent prosthesis, which is attached to the abutment with cement or with a fastener, for example. Alternative single stage implants with integral emergence profiles or one-piece implants with integral abutments may be used that extend through the transgingival layer so that the gingiva need not be reopened to access the implant.

Patients prefer to leave after initial surgery with some type of restoration and healing of both soft and hard tissue may be improved if the implant is loaded after surgery. Post-surgical loading, even if less than a full load of occlusion, however, is sufficient to displace the implant. Thus, threads may be used to secure the implant directly to the bone to achieve initial stability.

One way to improve osseointegration onto an implant, and in turn improve the long term stability of the implant, is to provide a porous material on the implant that the bone can grow into. Such a porous material may also increase short term stability for immediate loading due to a large friction coefficient with surrounding bone. Providing a porous material only on the surface of the implant, however, results in bone growth only near the surface of the implant. The final stability of the implant would be significantly increased if bone growth extends deeper than just near the surface of the implant. Such a porous structure, however, may not provide sufficient strength to use as threads on a screw-type implant to resist mastication forces. Thus, a porous implant is desired that provides sufficient initial and long-term stability when embedded in biological tissue, such as bone.

DETAILED DESCRIPTION

Figure 1:
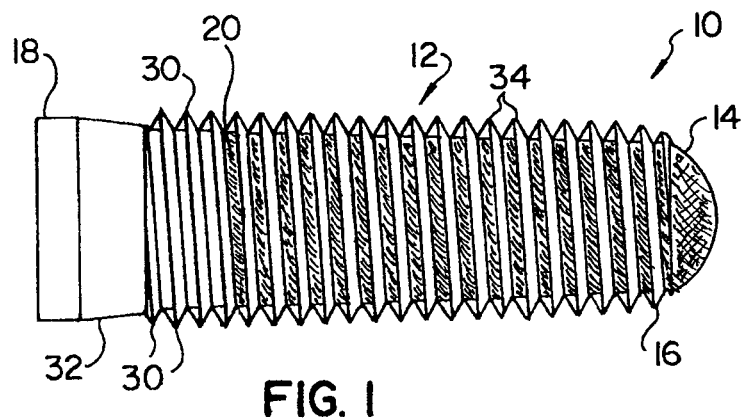
FIG. 1 is an elevational view of a dental implant in accordance with the present invention.
Figure 2:
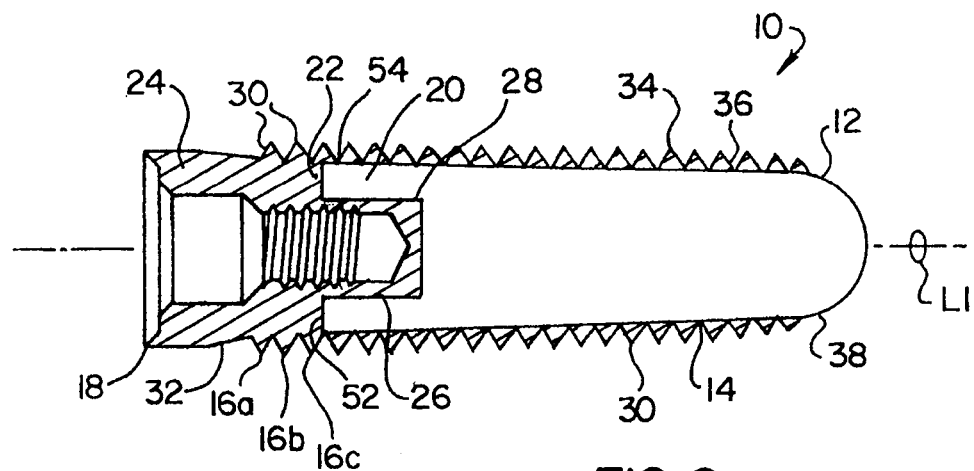
FIG. 2 is a cross-sectional view of the dental implant of FIG. 1 in accordance with the present invention.
Figure 3:
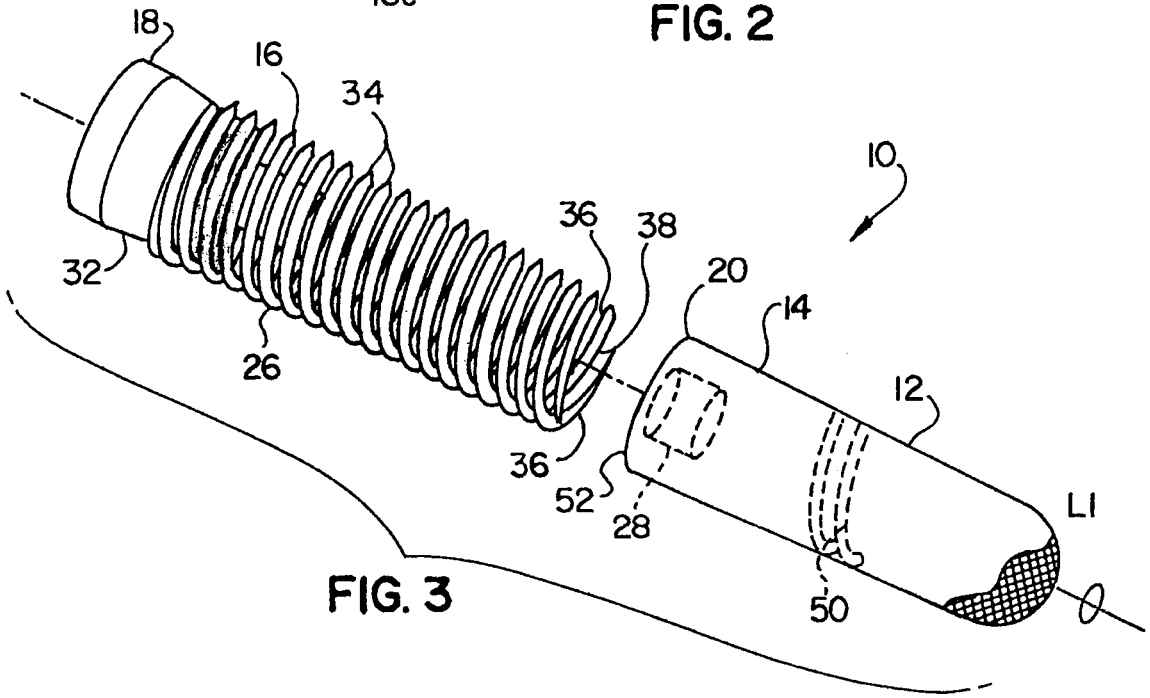
FIG. 3 is an exploded view of the dental implant of FIG. 1 in accordance with the present invention.

Referring to FIGS. 1-3, an implant 10 may be used to anchor prosthetic devices to bone. In one form, implant 10 is a dental implant for anchoring an abutment or other dental prosthesis to a jaw bone. The implant 10 generally defines a longitudinal axis L1 (shown in FIG. 2) and includes a shaft 12 made of a porous material for improving osseointegration onto the implant 10 as explained in greater detail below. The shaft 12 has an exterior surface 14 and at least one non-porous thread 16 winding around, and engaging, the exterior surface 14, and extending outwardly from the exterior surface 14 for engaging bone. While the illustrated shaft 12 is substantially porous, shaft 12 could have a non-porous, axially extending core. Such a core could be made of titanium, ceramic or other non-porous material.

Implant 10 includes a non-porous head portion 18 located at a coronal end portion 20 of the shaft 12. The non-porous head portion 18 is made of a suitable biocompatible material, such as titanium, although the head portion may also be made of other biocompatible materials such as at least one of the following: titanium alloy, stainless steel, zirconium, cobalt-chromium molybdenum alloy, ceramic, a polymer, and a composite material.

Referring to FIG. 2, the head portion 18 forms an axial bore 22 for receiving the bottom of an abutment and/or an abutment connector extending out of the abutment to secure the abutment to the implant 10. For this purpose, the bore 22 is internally threaded to receive the abutment connector, and has an anti-rotational flat or surface 24 (such as a hexagon, for example) to receive a corresponding interface from the abutment.

The head portion 18 has an apical extension 26 to contain the bore 22 entirely in the stronger, solid material of the head portion 18 rather than the porous material at the shaft 12. The exterior exposure of the porous material is then maximized by placing the extension 26 in a coronally accessible cavity 28 formed at the coronal end portion 20 of the shaft 12. Alternatively to the bore 22, the head portion 18 may provide a male interface for a separate female abutment. In this case, although the extension is not needed to form a bore, it may be used, nevertheless, to provide extra surface area for the shaft 12 to be press-fit against the head portion 18. In yet another alternative, the implant 10 may be a one-piece implant where the head portion 18 also includes an integral abutment or the implant 10 may be a single-stage dental implant with an integral transmucosal portion.

In the illustrated form, the helical thread 16 includes three helical parallel threads 16a, 16b, and 16c although more or less may be provided. One or more coils 30 of the threads 16a, 16b, and 16c are formed integrally with a main body 32 forming the head portion 18. The threads 16a, 16b, and 16c extend and wind apically away from the main body 32 concentric to longitudinal axis L1, and form uniformly spaced coils or rotations 34 as it extends axially along shaft 12.

The non-porous thread 16 has a helical, interior surface 36 that faces the shaft 12 and defines a central opening 38 configured for receiving the shaft 12 by at least a press-fit. Due to the porous material, the exterior surface 14 of the shaft 12 has a sufficient coefficient of friction with the interior surface 36 to restrict axial motion of the shaft 12 relative to the thread 16. Additionally, the exterior surface 14 of the shaft may define a helical groove 50 (shown in dashed line) for receiving the helical thread 16 to further restrict motion between the shaft 12 and thread 16.

While the head portion 18 and the non-porous thread 16 secure the shaft 12 without other devices, it will be appreciated, however, that the shaft 12 could additionally be attached to the head portion 18 using other mechanisms, such as adhesive, welding, diffusion bonding, sintering, fasteners and so forth.

The coronal end portion 20 of the shaft 12 is annular and extends between the apical extension 26 of the head portion 18 and the threads 16 for a tight press-fit between the two structures. In one form, this configuration will maintain an annular coronal face 52 of the coronal end portion 20 abutted against an annular, apically-facing shoulder 54 (FIG. 2) formed by the head portion 18 and facing the central opening 38.

The thread 16 may be integrally formed with the head portion 18, or attached to the head portion 18 by other bonding processes. The thread 16 may be made of the same material as the head portion 18 as described above. In one form, the thread 16 is made of titanium. The head portion 18 may be manufactured by using a screw-machine, or similar device, to machine the head portion. Wire electrical discharge machining (EDM) is used to cut the thread 16 without imparting any cutting loads to the thread 16, thereby maintaining the shape of the helical thread.

With the configuration described, the exterior surface 14 of the shaft 12 will be exposed as a spiraling surface between coils 34 of the thread 16 to receive osseointegrating bone. Osseointegration occurs and bone growth extends deeper on the shaft 12 than the surface 14 of the shaft 12, and the bone is free to grow anywhere within the shaft when the shaft 12 is substantially porous.

The shaft 12 is made of a porous material. An example of such a material is produced using TRABECULAR METAL™ technology generally available from Zimmer, Inc., of Warsaw, Ind. TRABECULAR METAL™ is a trademark of Zimmer Technology, Inc. Such a material may be formed from a reticulated vitreous carbon foam substrate which is infiltrated and coated with a biocompatible metal, such as tantalum, etc., by a chemical vapor deposition ("CVD") process in the manner disclosed in detail in U.S. Pat. No. 5,282,861, the disclosure of which is incorporated herein by reference. Other metals such as niobium, or alloys of tantalum and niobium with one another or with other metals may also be used.

Figure 4:
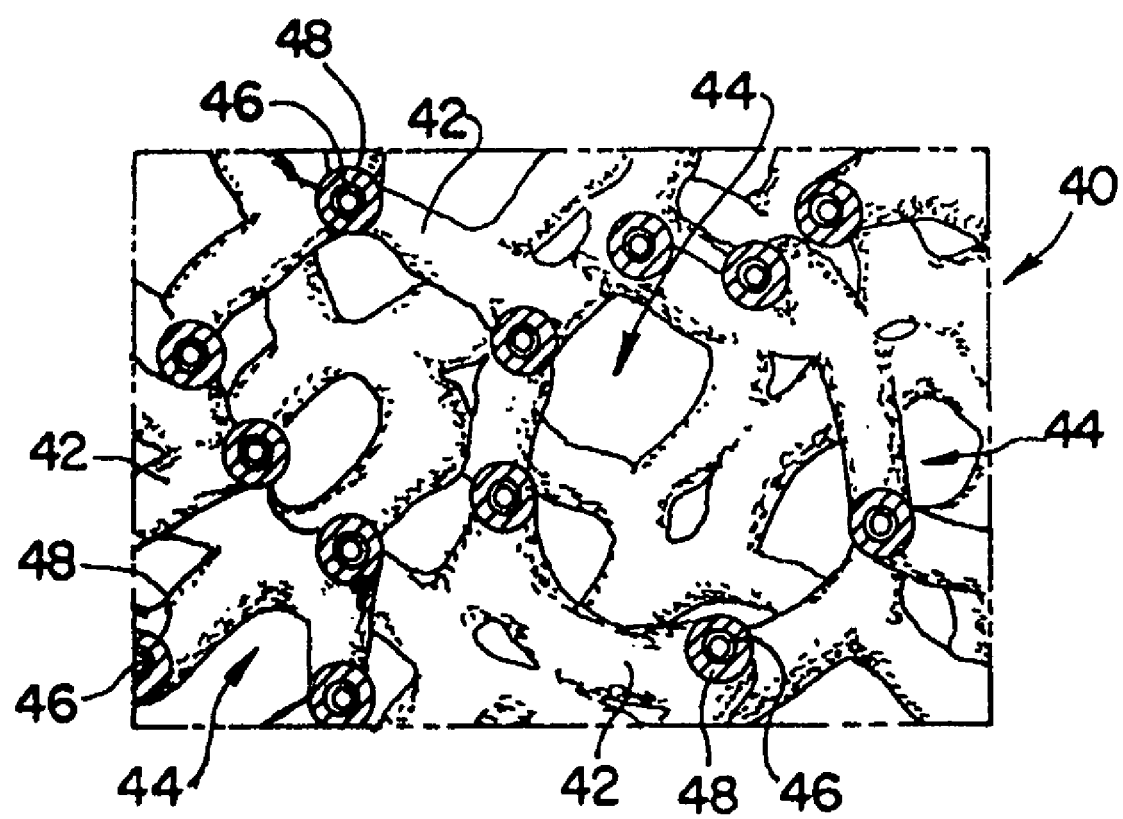
FIG. 4 is an enlarged fragmentary view of the portion of the porous tantalum forming the dental implant of FIG. 1 in accordance with the present invention.

Generally, as shown in FIG. 4, porous tantalum structure 40 includes a large plurality of ligaments 42 defining open spaces 44 therebetween, with each ligament 42 generally including a carbon core 46 covered by a thin film of metal 48 such as tantalum, for example. The open spaces 44 between ligaments 42 form a matrix of continuous channels having no dead ends, such that growth of cancellous bone through porous tantalum structure 40 is uninhibited. The porous tantalum may include up to 75%-85% or more void space therein. Thus, porous tantalum is a lightweight, strong porous structure which is substantially uniform and consistent in composition, and closely resembles the structure of natural cancellous bone, thereby providing a matrix into which cancellous bone may grow to anchor implant 10 into the surrounding bone of a patient's jaw, which increases the stability of the implantation. The rough exterior surface of such porous metal shaft provides a relatively high friction coefficient with adjacent bone forming the bore that receives the implant to further increase initial stability in addition to that provided by the thread 16. This structure can produce superior esthetic results by restricting movement of the implant.

Porous tantalum structure 40 may be made in a variety of densities in order to selectively tailor the structure for particular applications. In particular, as discussed in the above-incorporated U.S. Pat. No. 5,282,861, the porous tantalum may be fabricated to virtually any desired porosity and pore size, and can thus be matched with the surrounding natural bone in order to provide an improved matrix for bone ingrowth and mineralization. This includes a gradation of pore size on a single implant such that pores are larger on an apical end to match cancellous bone and smaller on a coronal end to match cortical bone, or even to receive soft tissue ingrowth. Also, the porous tantalum could be made denser with fewer pores in areas of high mechanical stress. Instead of smaller pores in the tantalum, this can also be accomplished by filling all or some of the pores with a solid material which is described in further detail below.

To provide additional initial mechanical strength and stability to the porous structure, the porous structure may be infiltrated with a filler material such as a non-resorbable polymer or a resorbable polymer. Examples of non-resorbable polymers for infiltration of the porous structure may include a polyaryl ether ketone (PAEK) such as polyether ketone ketone (PEKK), polyether ether ketone (PEEK), polyether ketone ether ketone ketone (PEKEKK), polymethylacrylate (PMMA), polyetherimide, polysulfone, and polyphenolsulfone.

Examples of resorbable polymers may include polylactic co-glycolic acid (PLGA), polylactic acid (PLA), polyglycolic acid (PGA), polyhydroxybutyrate (PHB), and polyhydroxyvalerate (PHV), and copolymers thereof, polycaprolactone, polyanhydrides, and polyorthoesters. By providing additional initial mechanical strength and stability with a resorbable filler material, a titanium reinforcing implant core may not be required. The resorbable material would resorb as the bone grows in and replaces it, which maintains the strength and stability of the implant.

With this porous structure, in one form, implant 10 is approximately 3.7 mm or greater in order to sustain intraoral mechanical forces. Implant 10 may have a generally cylindrical outer surface or may taper so that its diameter increases as it extends coronally to further increase friction with bone within a bore in the patient's jaw receiving the implant.

In use, implant 10 may be screwed into a bore drilled into a patient's jaw bone at an edentulous site to provide a firm initial seating of implant 10 into the bore. Thereafter, the bone tissue surrounding implant 10 may osseointegrate into the open spaces 44 of the porous metal shaft 12, thereby firmly anchoring shaft 12 and implant 10 into the surrounding bone structure. This also provides a favorable environment for load transfer to the bone since the porous material has a stiffness similar to that of cancellous bone. Consequently, this will stimulate more complete and stronger bone growth around the implant.

While implant 10 is used as a dental implant, it will be understood that the structure of an implant with a porous metal or porous tantalum portion press fit into helical threads may be used anywhere on an animal or human body.

It will also be appreciated that instead of, or in addition to, porous tantalum or porous metal, a shaft may be made of a first material that promotes bone growth or strengthens the implant instead of porous tantalum such as organic bone graft (e.g., autograft, allograft, xenograft), resorbable polymer (e.g., polylactic co-glycolic acid (PLGA), polylactic acid (PLA), polyglycolic acid (PGA), polyhydroxybutyrate (PHB), and polyhydroxyvalerate (PHV)), non-resorbable polymer, synthetic bone material such as hydroxyapatite (HA), or collagen. A shaft of such material may be initially formed and then press-fit into a thread of a different material, as described above, or the thread may be formed on the shaft in other ways.

While this invention has been described as having a preferred design, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. An implant, comprising:
a shaft having an apical end, a coronal end and an exterior surface, the entire exterior surface of the shaft being formed of a first material that is substantially porous;
a head portion having a main body with an apical end and a coronal end; and
a coil of threads having an apical end, a coronal end and an interior surface, and being made of a second material that is different from the first material, wherein the coronal end of the coil of threads is connected to the apical end of the main body and the coil of threads extends apically from the main body, with the interior surface of the coil engaging and winding around the exterior surface of the shaft, and extending outwardly from the exterior surface for engaging bone, with the interior surface of the coil of threads disposing the coronal end of the shaft proximate the apical end of the main body.

2. The implant of claim 1, wherein the second material from which the coil of threads is made is substantially non-porous.

3. The implant of claim 1, wherein the first material includes tantalum.

4. The implant of claim 1, wherein the first material comprises at least one of an organic bone graft, a resorbable polymer, a non-resorbable polymer, synthetic bone material, and collagen.

5. The implant of claim 1, wherein the head portion comprises at least one of titanium, titanium alloy, stainless steel, zirconium, cobalt-chromium molybdenum alloy, ceramic, a polymer, and a composite material.

6. The implant of claim 1, wherein the shaft has a coronal bore and the main body has an apical extension, and wherein the apical extension is disposed within the coronal bore when the shaft is disposed within the coil of threads.

7. The implant of claim 6, wherein the apical extension of the main body is pressed fit into the coronal bore of the shaft.

8. The implant of claim 1, wherein the coronal end of the coil of threads is integrally formed with the apical end of the main body of the head portion.

9. The implant of claim 1, wherein the coil of threads maintains the shaft in engagement with the main body of the head portion.

10. The implant of claim 1, wherein the coil of threads and the head portion are made from the same material.

11. The implant of claim 1, wherein the coil of threads is helical and defines a central opening configured for receiving the coronal end of the shaft.

12. The implant of claim 1, wherein the coil of threads is configured to engage the exterior surface of the shaft by at least a press-fit.

13. The implant of claim 1, wherein the coil of threads is secured to the shaft with sufficient friction to restrict axial motion of the shaft relative to the coil of threads.

14. The implant of claim 1, wherein the exterior surface of the shaft defines a helical groove for receiving the coil of threads.

15. The implant of claim 1, wherein the implant is a dental implant.

16. The implant of claim 1, wherein the coil of threads comprises three coils of threads each having an apical end, a coronal end connected to the apical end of the main body, and an interior surface, wherein each of the coils of threads extends apically from the main body with the interior surfaces of the coils engaging and winding around the exterior surface of the shaft.

17. A dental implant, comprising:
a shaft having an apical end, a coronal end and an exterior surface, the entire exterior surface of the shaft being formed of a metallic and substantially porous material;
a head portion having a main body with an apical end and a coronal end; and
a helical thread having an apical end and a coronal end, wherein the coronal end of the helical thread is connected to the apical end of the main body and the helical thread extends apically from the main body, and with the helical thread generally defining a central opening receiving the shaft and securing the shaft in at least a press-fit within the helical thread, with the helical thread disposing the coronal end of the shaft proximate the apical end of the main body.

18. The dental implant of claim 17, wherein the shaft is porous and the thread is non-porous.

19. The dental implant of claim 17, wherein the head portion comprises a non-porous head portion.

20. The dental implant of claim 19, wherein the main body of the head portion includes an apical extension press fit into a coronal bore of the shaft.

21. The dental implant of claim 17, wherein the helical thread maintains the shaft in engagement with the head portion.

22. The dental implant of claim 17, wherein the helical thread is integrally formed with the head portion.

23. The dental implant of claim 17, wherein the helical thread has a spiraling interior surface generally defining the central opening for facing and engaging the shaft.

24. A method of assembling an implant comprising:
providing a head portion having a main body with an apical end and a coronal end, and a helical thread having an apical end and a coronal end, wherein the coronal end of the helical thread is connect to the apical end of the main body and the helical thread extends apically from the main body, with the helical thread defining a central opening;
providing a shaft having an apical end, a coronal end and an exterior surface, with the entire exterior surface being formed of a metallic and substantially porous material; and
inserting the porous shaft into the central opening formed by the helical thread, with the helical thread engaging and winding around the exterior surface of the shaft and the helical thread disposing the coronal end of the shaft being proximate the apical end of the main body.

25. The method of claim 24, wherein the helical thread is formed of a non-porous material.

26. The method of claim 24, wherein the shaft is press-fit into the central opening.

* * * * *